US00PP37807P2

(12) United States Plant Patent
Hartman

(10) Patent No.: US PP37,807 P2
(45) Date of Patent: Oct. 20, 2026

(54) ***CALADIUM* PLANT NAMED 'VIC 3-69'**

(50) Latin Name: ***Caladium* X *hortulanum***
Varietal Denomination: VIC 3-69

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 19/639,786

(22) Filed: Apr. 6, 2026

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP33,558 P2 * 10/2021 Hartman ..... Plt./373

* cited by examiner

*Primary Examiner* — Karen M Redden
(74) *Attorney, Agent, or Firm* — C. Anne Whealy

(57) ABSTRACT

A new and distinct cultivar of *Caladium* plant named 'VIC 3-69', characterized by its upright and mounding plant habit and relatively short in height; dense, leafy and bushy appearance; vigorous growth habit and rapid growth rate; rugose lance-type leaves that are mostly medium green in color with pink-colored venation surrounded by lighter pink interveinal areas and medium green-colored margins; and petioles that are tannish pink in color with brown-colored stripes.

4 Drawing Sheets

Figure 1:
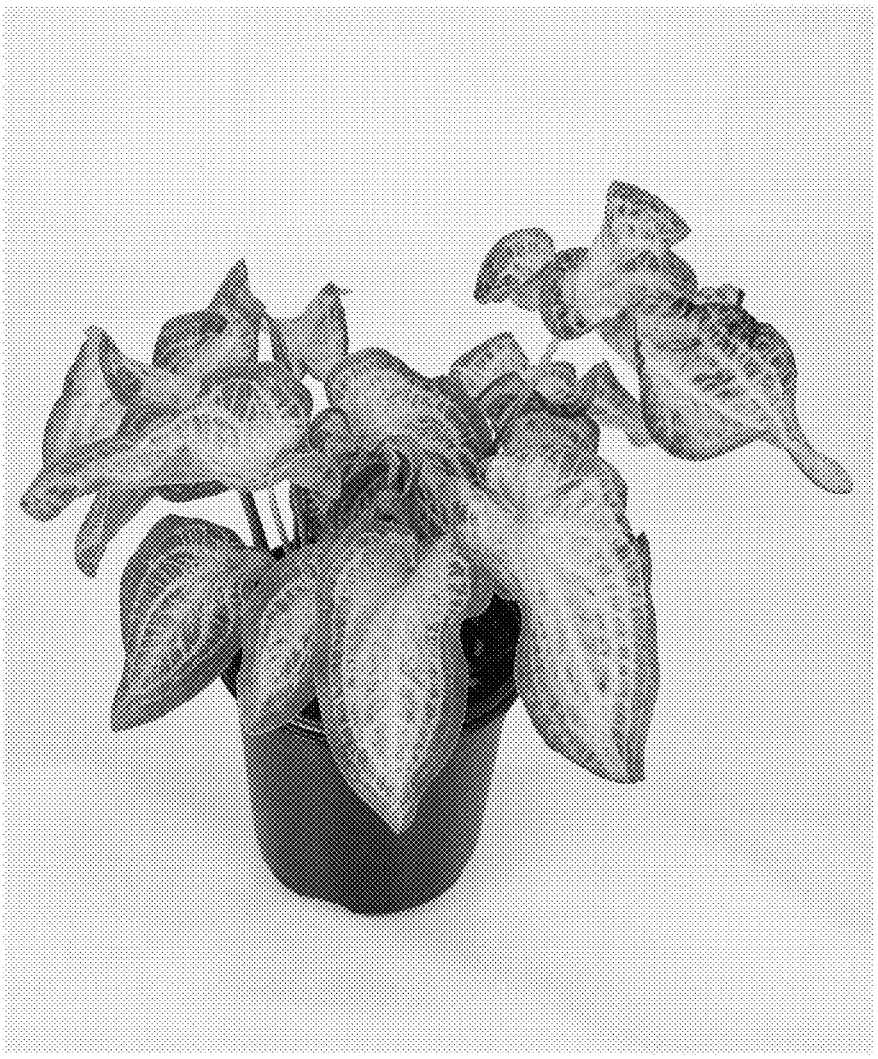

Botanical designation: *Caladium* X *hortulanum*.
Cultivar denomination: 'VIC 3-69'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'VIC 3-69'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2017 in Avon Park, Florida of *Caladium* X *hortulanum* 'Victoria', disclosed in U.S. Plant Pat. No. 18,087, as the female, or seed, parent with *Caladium* X *hortulanum* 'Tickle Me Pink', disclosed in U.S. Plant Pat. No. 31,061, as the male, or pollen, parent. The new *Caladium* plant was discovered and selected by the Inventor as a single plant within the progeny of the stated cross-pollination in a controlled outdoor nursery environment in Avon Park, Florida in September, 2018.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April, 2019 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'VIC 3-69'. These characteristics in combination distinguish 'VIC 3-69' as a new and distinct *Caladium* plant:

1. Upright and mounding plant habit and relatively short in height; dense, leafy and bushy appearance.
2. Vigorous growth habit and rapid growth rate.
3. Rugose lance-type leaves that are mostly medium green in color with pink-colored venation surrounded by lighter pink interveinal areas and medium green-colored margins.
4. Petioles that are tannish pink in color with brown-colored stripes.

Plants of the new *Caladium* differ primarily from plants of the female parent, 'Victoria', in leaf color as plants of the new *Caladium* are mostly medium green in color with pink-colored venation surrounded by lighter pink interveinal areas and medium green-colored margins whereas leaves of plants of 'Victoria' are rose pink in color suffused with greenish white with rose pink venation.

Plants of the new *Caladium* differ primarily from plants of the male parent, 'Tickle Me Pink', in the following characteristics:

1. Leaves of plants of the new *Caladium* are more rugose than and have more undulating margins than leaves of plants of 'Tickle Me Pink'.
2. Leaves of plants of the new *Caladium* are mostly medium green in color with pink-colored venation surrounded by lighter pink interveinal areas and medium green-colored margins whereas leaves of plants of 'Tickle Me Pink' have dark green-colored margins, rose red venation and interveinal areas that are green, tan green and rose red mosaic.

Plants of the new *Caladium* can be compared to plants of *Caladium* X *hortulanum* 'Blushing Bride', disclosed in U.S. Plant Pat. No. 22,213. In side-by-side comparisons, plants of the new *Caladium* differ primarily from plants of 'Blushing Bride' in the following characteristics:

1. Leaves of plants of the new *Caladium* are more rugose than and have more undulating margins than leaves of plants of 'Blushing Bride'.
2. Leaves of plants of the new *Caladium* are mostly medium green in color with pink-colored venation surrounded by lighter pink interveinal areas and medium green-colored margins whereas leaves of plants of 'Blushing Bride' are greyed purple in color with dark green-colored margins and whitish-colored venation tinged with greyed purple.

Plants of the new *Caladium* can be compared to plants of *Caladium* X *hortulanum* 'Flare', disclosed in U.S. Plant Pat. No. 25,426. In side-by-side comparisons, plants of the new *Caladium* differ primarily from plants of 'Flare' in the following characteristics:

1. Leaves of plants of the new *Caladium* are more rugose than and have more undulating margins than leaves of plants of 'Flare'.
2. Leaves of plants of the new *Caladium* are mostly medium green in color with pink-colored venation surrounded by lighter pink interveinal areas and medium green-colored margins whereas leaves of plants of 'Flare' have rose red-colored centers surrounded by a greyed green and pink-colored speckling and dark green-colored margins.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'VIC 3-69' grown in a container that has not had its tuber de-eyed prior to planting.

Figure 2:
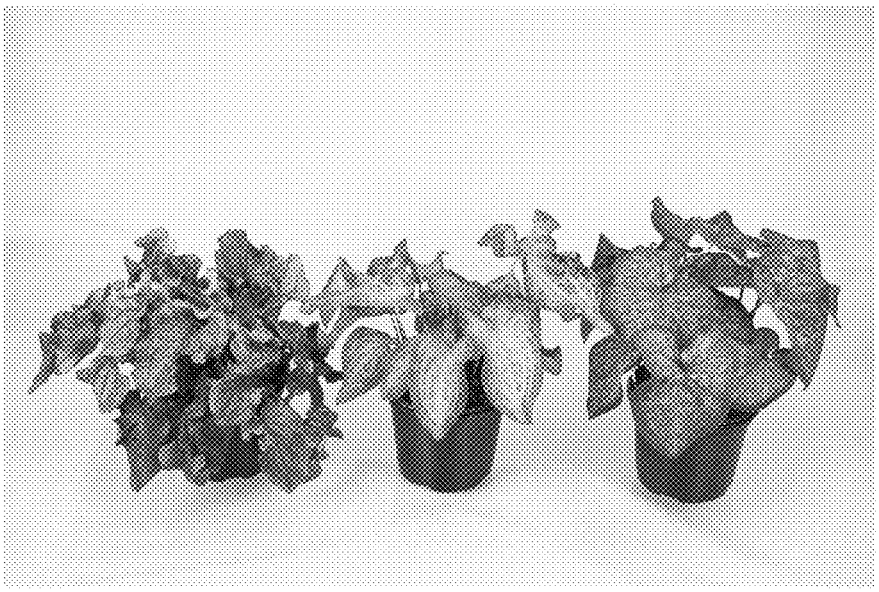

The photograph at the top of the second sheet (FIG. 2) is side perspective view of typical plants of the female parent, 'Victoria' (left), 'VIC 3-69' (center) and the male parent, 'Tickle Me Pink' (right).

Figure 3:
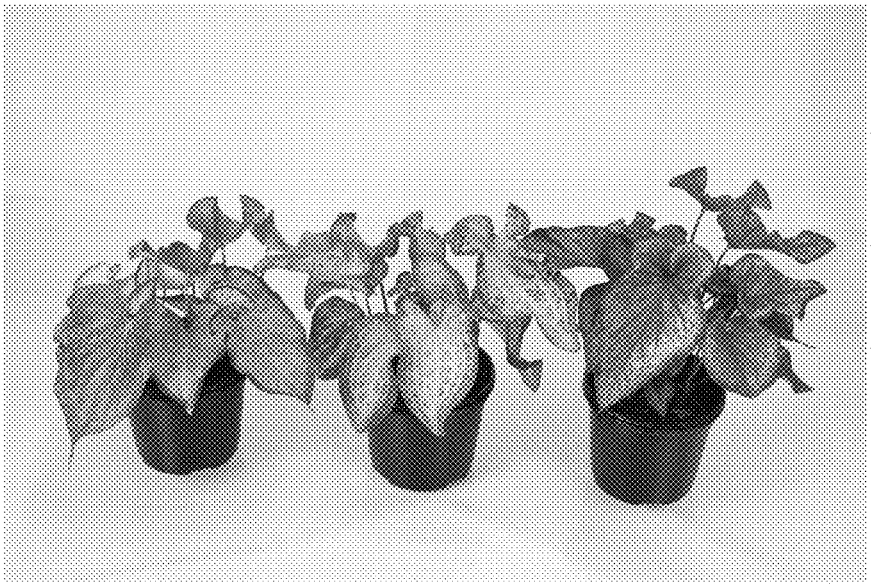

The photograph at the bottom of the second sheet (FIG. 3) is side perspective view of typical plants of 'Flare' (left), 'VIC 3-69' (center) and 'Blushing Bride' (right).

Figure 4:
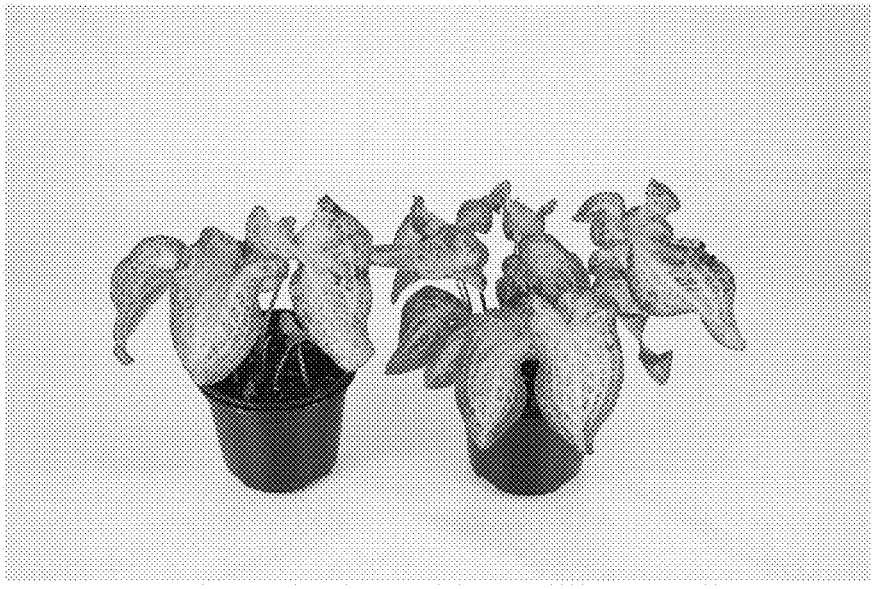

The photograph at the top of the third sheet (FIG. 4) is a comparison view of typical plants of 'VIC 3-69' grown in containers, the plant on the left has not had its tuber de-eyed and the plant on the right has had its tuber de-eyed prior to planting.

Figure 5:
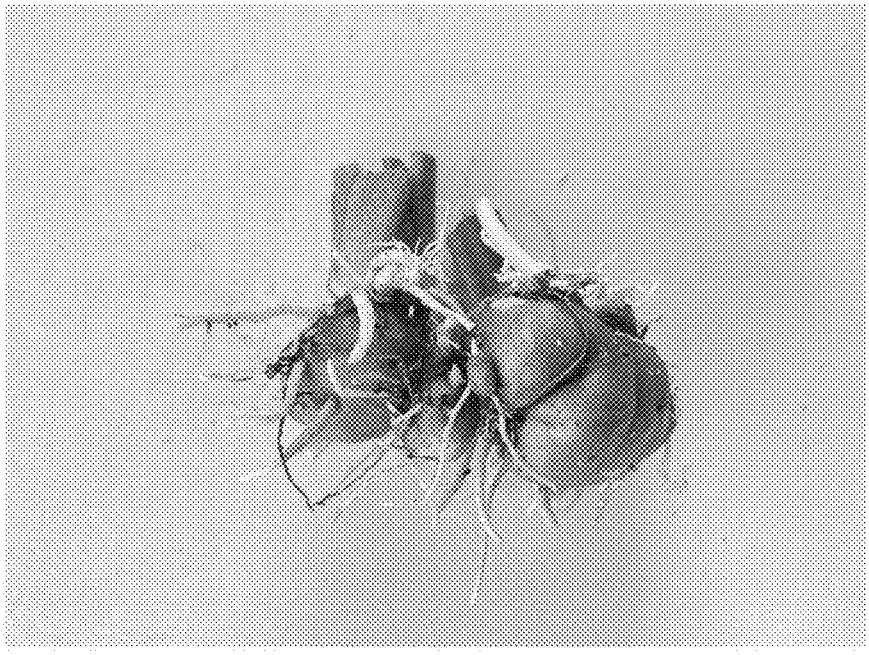

The photograph at the bottom of the third sheet (FIG. 5) is a close-up view of freshly-harvested tubers with roots of 'VIC 3-69'.

Figure 6:
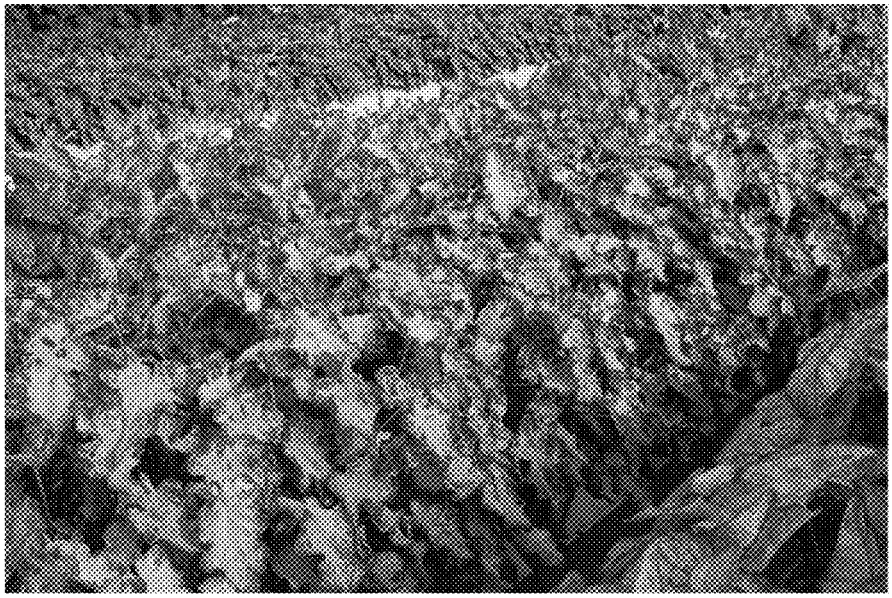

The photograph at the top of the fourth sheet (FIG. 6) is a side perspective view of typical field-grown plants of 'VIC 3-69'.

Figure 7:
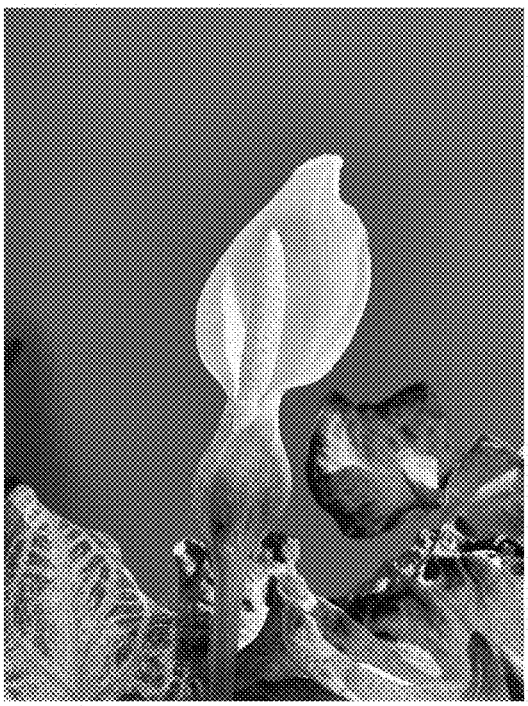

The photograph at the bottom of the fourth sheet (FIG. 7) is a close-up view of a typical inflorescence of 'VIC 3-69'.

DETAILED BOTANICAL DESCRIPTION

The aforementioned photographs and following observations and measurements describe plants grown in 15-cm containers in a polypropylene-covered shade house (50% light reduction) in Avon Park, Florida and plants grown in ground beds under full sunlight conditions in an outdoor nursery in Zolfo Springs, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and levels were about 1,300 μmol. During the production of the outdoor nursery-grown plants, day temperatures ranged from about 29° C. to 35° C., night temperatures ranged from about 23° C. to 26° C. and under full sunlight conditions. Plants grown in the shade house were about nine weeks old and plants grown in the outdoor nursery were about seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'VIC 3-69'.

Parentage:

*Female, or seed, parent.*—*Caladium* X *hortulanum* 'Victoria', disclosed in U.S. Plant Pat. No. 18,087.

*Male, or pollen, parent.*—*Caladium* X *hortulanum* 'Tickle Me Pink', disclosed in U.S. Plant Pat. No. 31,061.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented and branched; individual segments are elliptic to irregular in shape. Height: About 2.9 cm to 3.5 cm. Diameter, largest width: About 5 cm to 9.1 cm. Segment height: About 2.7 cm. Segment diameter: About 3.3 cm to 3.7 cm. Axillary bud shape: Roughly triangular, flattened, somewhat elliptic. Axillary bud height: About 5 mm. Axillary bud width: About 6 mm. Texture: Thick, starchy; somewhat brittle. Color: Periderm, freshly-harvested: Close to 199B with flecks, close to N199A. Periderm, dried: Close to 200A. Epidermis: Close to 155B, 155D and 159A. Cortical tissue: Close to 159B and 159C. Axillary buds: Close to 36C and 38D. Root description: Relatively thick, fleshy contractile roots with few lateral branches; color, close to NN155D; actual color of the roots is dependent on substrate composition, water quality, fertilizer type and formulation, substrate temperature and physiological age of roots; root density, moderate.

Plant description:

*Plant type*.—Herbaceous perennial; suitable as a potted plant in containers 15-cm to 25-cm and suitable as a landscape plant in shaded landscape areas.

*Plant and growth habit*.—Upright and mounding plant habit and relatively short in height; dense, leafy and bushy appearance; vigorous growth habit and rapid growth rate; potted plants finish in saleable form in about six to seven weeks after planting tubers; leaf petioles and leaves arise from one or more growing points on tubers; leaf petioles initially upright and leaning outwardly to arching with development.

*Plant height, from soil level to top of foliar plane, shade house-grown potted plants, tubers de-eyed*.—About 15.5 cm to 22 cm.

*Plant height, from soil level to top of foliar plane, shade house-grown potted plants, tubers not de-eyed*.—About 15 cm to 20 cm.

*Plant height, from soil level to top of inflorescences*.—About 38 cm.

*Plant diameter, shade house-grown potted plants, tubers de-eyed*.—About 22 cm to 31 cm.

*Plant diameter, shade house-grown potted plants, tubers not de-eyed*.—About 28 cm to 31 cm.

*Number of shoots per plant, shade house-grown potted plants, tubers de-eyed*.—About four to five develop per #1 tuber.

*Number of shoots per plant, shade house-grown potted plants, tubers not de-eyed*.—About three to four develop per #1 tuber.

*Cataphylls, shade house-grown potted plants*.—Length: About 5.2 cm to 7.7 cm. Width: About 1.3 cm to 1.7 cm. Shape: Wedge-shaped or lanceolate. Apex: Acute to acuminate. Base: Sheathing the stem. Texture, outer and inner surfaces: Smooth, glabrous. Color, outer surface: Close to 156D tinged with close to 199D with stippling and streaks, close to 200A and 200B; fading to 199D with subsequent development. Color, inner surface: Close to N155D; colors and patterns on outer surface are visible on inner surface.

Leaf description:

*Arrangement and type*.—Alternate; simple; lance-type.

*Length, shade house-grown potted plants, tubers de-eyed*.—About 12 cm to 18 cm.

*Width, shade house-grown potted plants, tubers de-eyed*.—About 7 cm to 10.1 cm; when flattened, about 7.5 cm to 12 cm.

*Shape*.—Ovate.

*Apex*.—Acute to somewhat obtuse.

*Base*.—Sagittate-peltate or cordate, lobes often imbricate.

*Margin*.—Entire, with broad undulations.

*Texture and luster, upper surface*.—Rugose, glabrous; dull sheen.

*Texture and luster, lower surface*.—Rugose, glabrous; slightly glaucous in center and around venation, dull sheen.

*Venation pattern*.—Pinnate and palmate.

*Color, shade house-grown potted plants*.—Developing leaves, upper surface: Interveinal areas: Central pink areas, close to 65A to 65D; green areas, close to 137A suffused with close to 147D and 184C; towards the margins, occasional areas of close to 177D and 182D. Margins: Close to NN137A suffused with close to 148D. Basal notch: Close to 147D, 63C, 63D and 187B. Midvein: Close to 65A to 65C; surrounding the midvein, close to 65A to 65D. Lateral venation: Close to 65C; surrounding the veins, close to 65C and 65D. Developing leaves, lower surface: Interveinal areas: Central pink areas, close to 75D, 55D and 56A; green and white areas, close to 191B and N155C. Margins: Close to 191B; narrow marginal edges, close to 187B. Basal notch: Close to 148D tinged with close to 63D. Midvein: Close to N155B and N155C; surrounding the midvein, close to 75D and 56D. Lateral venation: Close to 195A; surrounding the veins, close to N155D. Fully expanded leaves, upper surface: Interveinal areas: Central pink areas, close to 65A to 65D; green areas, close to 137A suffused with close to 147D and 184C. Margins: Close to NN137A suffused with close to 148D; narrow marginal edges, close to 187B. Basal notch: Close to 147D, 63C, 63D and 187B. Midvein: Close to 65A to 65C; surrounding the midvein, close to 65A to 65D. Lateral venation: Close to 65B; surrounding the veins, close to 65A and 65B. Fully expanded leaves, lower surface: Interveinal areas: Central pink areas, close to 75D, 55D and 56A; green and white areas, close to 191B and N155C. Margins: Close to 191B; narrow marginal edges, close to 187B. Basal notch: Close to 148D tinged with close to 63D. Midvein: Close to N155B and N155C; surrounding the midvein, close to 75D and 56D. Lateral venation: Close to 147D and N155C; surrounding the veins, close to 75D and 56A.

*Petioles*.—Aspect: Initially upright and straight and leaning outwardly with development; flexible. Length, shade house-grown potted plants: About 14.2 cm to 22 cm. Diameter, distally, shade house-grown potted plants: About 3.4 mm to 5.2 mm. Diameter, proximally, shade house-grown potted plants: About 4 mm to 8 mm. Texture and luster: Smooth, glabrous; glaucous. Color, shade house-grown potted plants: When developing and developed: Close to 181D and 177D with stippling, stripes, streaks and tessellations, close to 200A and N200A; just below the leaf junction, close to 145C with less stippling, and fewer stripes and streaks, close to 200C; may be faintly tinged with close to N155B. Wing length, shade house-grown potted plants: About 2.3 cm to 4.4 cm. Wing diameter, shade house-grown potted plants: About 5 mm to 8.5 mm. Texture and luster, outer and inner surfaces: Smooth, glabrous; dull to slightly glossy. Wing color, shade house-grown potted plants: Outer surface: Close to 156D with stippling, streaks and marbling, close to N200A and 200A. Inner surface: Close to 196B; colors and patterns from the outer surface are visible on the inner surface.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about nine weeks after growth commences; inflorescences last about three days before fading; inflorescences persistent.

*Spathe*.—Length, overall: About 11.5 cm. Length, distal open portion: About 8.2 cm. Length, proximal closed portion: About 3.3 cm. Width, distal open portion: About 4.2 cm. Depth, distal open portion: About 2 cm. Width, at constriction: About 1.5 cm. Width, proximal closed portion: About 2.4 cm. Shape, open portion: Elliptic, obovate. Apex: Acute. Base: Acute. Margin: Entire, slightly reflexed. Texture and luster, front surface: Smooth, glabrous; dull sheen. Texture and luster, rear surface: Smooth, glabrous; distally, dull sheen; proximally, glaucous and dull sheen. Color, front surface: Distal open portion: Close to 155B; with subsequent development, color becoming closer to 199A and 200C. Proximal closed portion: Close to 148D, at the base, flushed with close to 187A; colors do not change with subsequent development. Color, rear surface: Distal open portion: Close to 145D; center, close to 150D tinged with close to 160D; colors do not change with subsequent development. Proximal closed portion: Close to 147C; streaks, close to 147D; colors do not change with subsequent development.

*Spadix*.—Length, overall: About 7.6 cm. Length, male flower zone (including sterile flowers): About 6 cm. Length, sterile zone: About 1.6 cm. Length, female flower zone: About 1.6 cm. Diameter, male flower zone: About 8 mm. Diameter, sterile flower zone: About 5 mm. Diameter, female flower zone: About 8 mm. Shape: Columnar, spindle-shaped. Apex: Acute. Base: Obtuse. Aspect: Upright. Color, mature, male zone: Close to 11C to 11D. Color, mature, sterile zone: Close to 159D. Color, mature, female zone: Stigmas, close to 155D; ovaries, close to 155C. Male flowers: Quantity per spadix: About 156. Shape: Obovate. Height: About 3.5 mm. Diameter: About 3.2 mm. Pollen amount: Abundant. Pollen color: Close to 10D. Female flowers: Quantity per spadix: About 120. Shape: Obovate. Height: About 3.5 mm. Diameter: About 2 mm. Stigma color: Close to 155D. Ovary color: Close to 155C.

*Scapes*.—Length: About 26.7 cm. Diameter: About 9 mm. Strength: Sturdy; flexible. Aspect: Mostly erect, straight. Texture and luster: Smooth, glabrous; proximally, slightly glossy; distally, slightly glaucous. Color: Close to 199D, with stippling, streaks and stripes, close to 147A and 147B tinged with close to N199A; distally, close to 147C and 147D tinged with close to 199D and with sparse streaks, close to N200A.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'VIC 3-69' as herein illustrated and described herein.

* * * * *